United States Patent [19]

Armstrong et al.

[11] Patent Number: 5,606,978
[45] Date of Patent: Mar. 4, 1997

[54] HEART MONITORING APPARATUS

[75] Inventors: David R. Armstrong, Welwyn, United Kingdom; Hendrick J. R. Van Eck, Maasdam, Netherlands

[73] Assignee: Hertford Medical Limited, Welwyn Garden City, United Kingdom

[21] Appl. No.: 367,307

[22] PCT Filed: Jul. 13, 1993

[86] PCT No.: PCT/GB93/01463

§ 371 Date: Jan. 13, 1995

§ 102(e) Date: Jan. 13, 1995

[87] PCT Pub. No.: WO94/01040

PCT Pub. Date: Jan. 20, 1994

[30] Foreign Application Priority Data

Jul. 13, 1992 [GB] United Kingdom ............ 9214818

[51] Int. Cl.$^6$ ........................... A61B 5/0402
[52] U.S. Cl. ........................... 128/711; 128/696
[58] Field of Search ........................... 128/711, 696

[56] References Cited

U.S. PATENT DOCUMENTS 4,909,260  3/1990  Salem et al. ............... 128/721
5,086,778  2/1992  Mueller et al. ............. 128/696
5,343,870  9/1994  Gallant ...................... 128/711

FOREIGN PATENT DOCUMENTS 346685  5/1989  European Pat. Off. .

Primary Examiner—Marvin M. Lateef
Assistant Examiner—Scott M. Getzow
Attorney, Agent, or Firm—Dilworth & Barrese

[57] ABSTRACT

An ambulatory heart monitoring apparatus (1) is provided with a slot (3) for receiving an IC card (2). A user places electrodes (7,8) on his body. Operation of a switch (5) causes the apparatus to record EGG signals from the electrodes (7,8) onto the IC card (2). Operation data, including, for example, battery voltage data, data representing the impedance between the electrodes (7,8) and calibration data, are stored on the IC card (2) in association with the recorded ECG signal. The operation data is useful for managing remote subjects. Also the calibration data can be used to normalize the recorded ECG data when it is processed at a remote processing station.

22 Claims, 4 Drawing Sheets

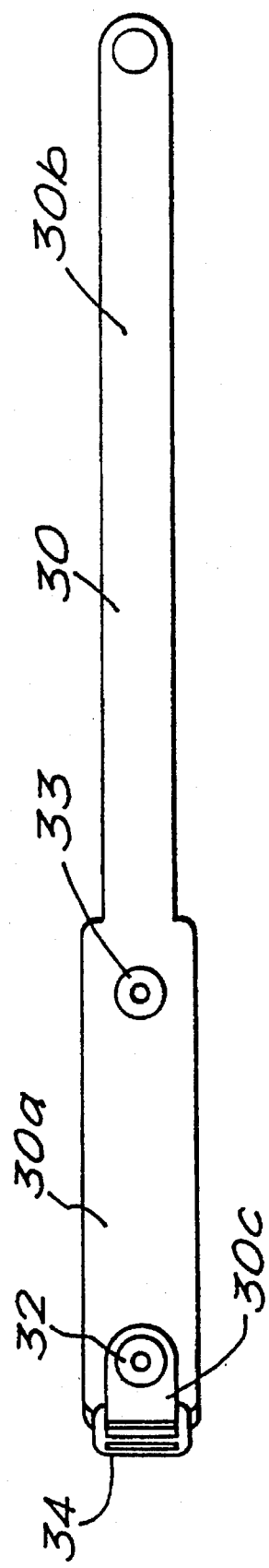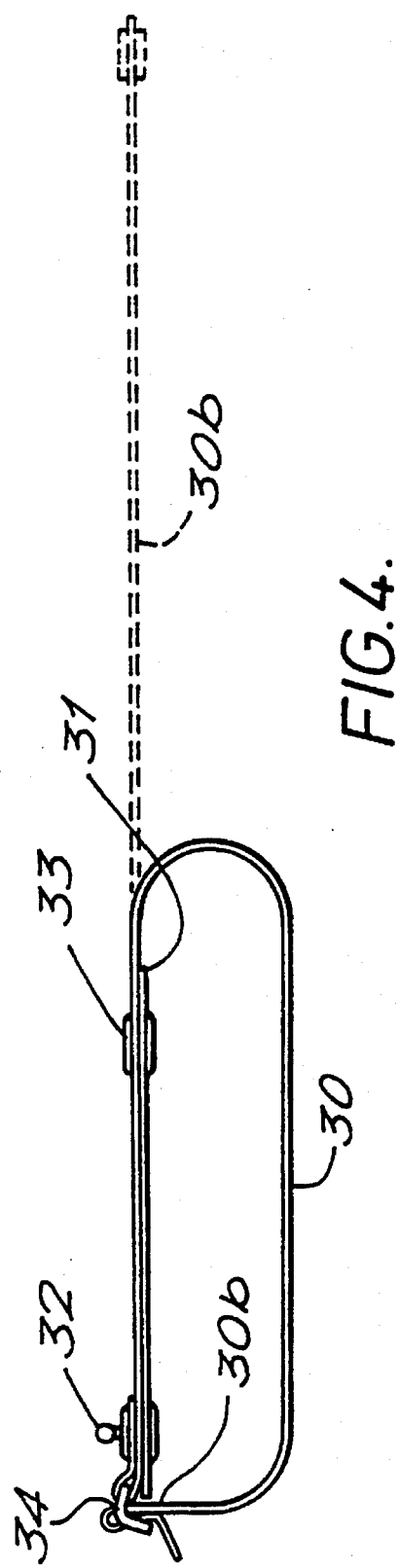

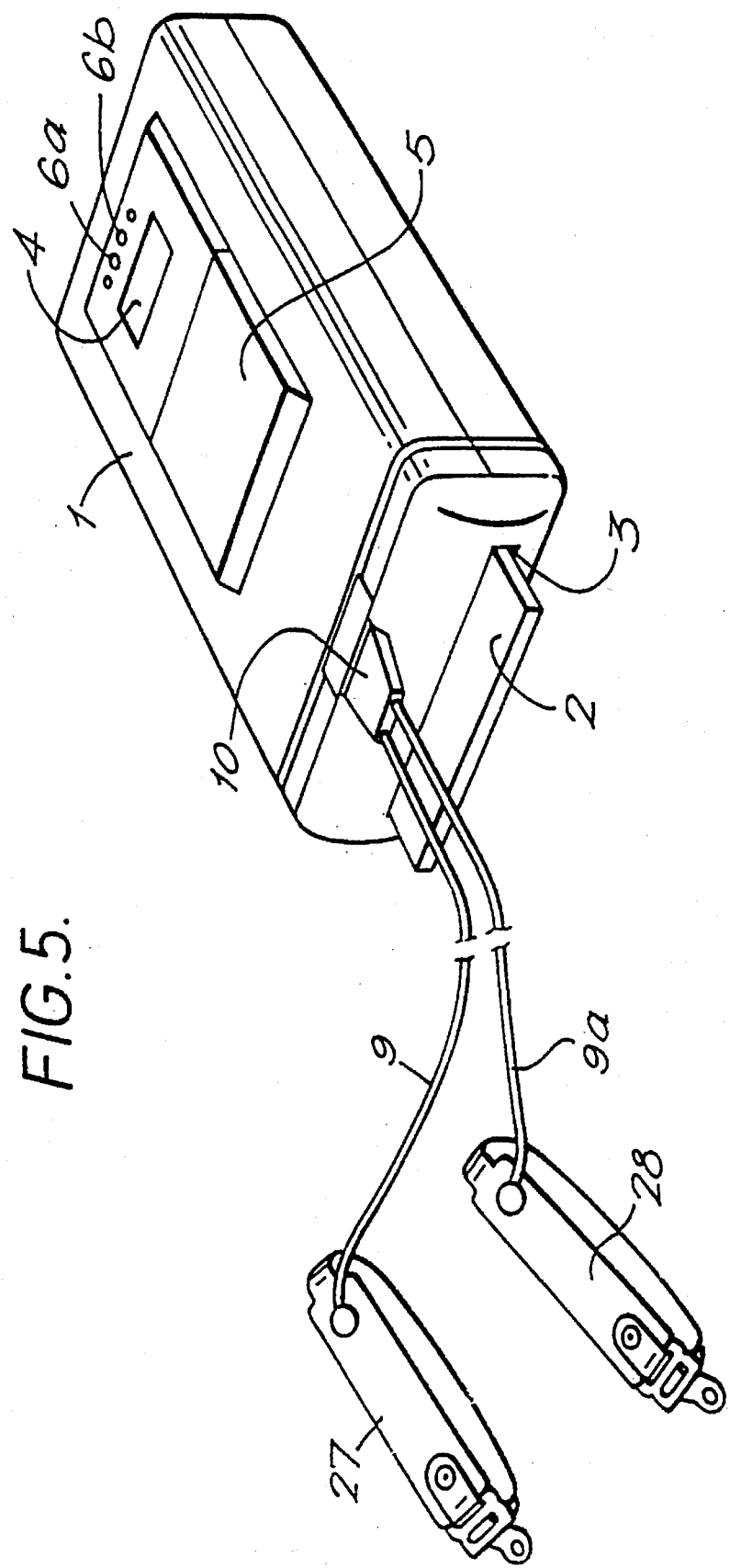

HEART MONITORING APPARATUS

FIELD OF THE INVENTION

The present invention relates to an ambulatory heart monitoring apparatus and a method of heart monitoring.

BACKGROUND TO THE INVENTION

During the testing of some new drugs, it is necessary to monitor the heart of a patient being treated with the new drug. It is inconvenient for an active patient to be kept in a controlled environment, such as a hospital, during the monitoring. Consequently, patients have been provided with heart monitoring equipment which they may take home with them. Such equipment comprises means for detecting an electrocardiographic (ECG) signal and a device for transmitting the detected signals through the public telephone network. If a patient begins to feel unwell or detects an abnormality in his heartbeat, he must dial a central station and instruct an operator, at the central station, to prepare to record a transmitted ECG signal. This system suffers from a number of disadvantages including the problem of language, since drug trials often take place across national boundaries, the non-availability of telephones and poor quality telephone lines. Also, drug companies are wary of becoming directly involved in patient care which is properly the domain of the patient's physician.

The aforementioned disadvantages may be overcome by replacing the telephone link by data storage media which may be posted to the central station. One known device is the CardioRam produced by Elmed Elektromedizinische Geräte. However, this device records ECG signals for a 24 hour period which makes it unsuitable for drug testing methodologies where intermittent recording is employed over extended periods, e.g. a month.

Another device is known from European Patent Application No. 346685 which is capable of intermittent recording of ECG signals.

None of the prior art IC card ambulatory heart monitoring apparatuses are entirely suitable for the purpose of apparatus embodying the present invention. It is intended that patients will use such apparatus unsupervised. This leads to the problem of ensuring that the patients use the apparatus properly and that the apparatus itself is functioning correctly.

It is an aim of the present invention to provide an ambulatory heart monitoring apparatus which is simple enough to meet the market demand at a reasonable cost, whilst providing high quality information on heart function.

SUMMARY OF INVENTION

According to a first aspect of the present invention, there is provided an ambulatory heart monitoring apparatus comprising: sensor means for detecting an electrocardiographic signal; interface means for receiving an IC card and for transferring data thereto; and control means responsive to operation of the user input means to cause a block of ECG data, derived from signals detected by the sensor means during a predetermined period, to be sent to the interface means for storage in an IC card, characterised by means for producing operation data as a function of an operational parameter of the apparatus wherein the control means causes the operation data to be sent to the interface means for storage in the IC card in association with the ECG data block.

IC card means a card shaped carrier incorporating at least one memory IC and includes smartcards.

The operation data can be characterised as being about the apparatus rather than about the patient. This is data which is useful to determine whether the apparatus is being used properly and functioning correctly.

Advantageously, the apparatus includes means for producing calibration data representive of the calibration state of the apparatus and the operation data includes the calibration data. Such data can be used to normalise ECG data to take account of variations between apparatuses or over time.

Conveniently, the apparatus is powered by a battery and includes battery voltage sensing means and the operation data includes data representing a sensed battery voltage. This data can be used to normalise ECG data, if necessary, or to provide an indication to the person analysing the data that a new battery should be fitted.

Conveniently, the sensor means includes two electrodes for contacting with the body of a subject and detecting means for detecting whether the electrodes are correctly contacting the body of a subject, and the operation data includes data indicative of whether the electrodes have correctly contacted the body of the patient during detection of an ECG signal. The electrodes may be of any convenient type. However, the apparatus may be provided with electrodes mounted directly thereon. The electrodes may then be positioned to respond to ECG signals by placing the body of the apparatus against the chest of a subject. This data can be used to normalise the ECG data or to indicate that a patient requires further tuition.

The detecting means may comprise an impedance measuring means for measuring the impedance between the electrodes. Preferably, the apparatus includes means whereby the impedance between the electrodes is measured at the start and the end of the predetermined period.

Preferably, the IC card is pre-programmed with data comprising a card ID, the card capacity and an IC card battery fitting date.

Data indicating the amount of storage space remaining on the card may be calculated by the apparatus and stored on the card when each new recording is made.

Preferably, control data is stored on the IC card for controlling the operation of the apparatus. Such data may comprise a recording duration and an ECG signal sampling rate.

Preferably, an instrument ID code is stored on the IC card, for example with each ECG data block.

In an embodiment, the control means is responsive to regime data from the interface means to cause a further block of ECG data to be sent to the interface means, the further block of ECG data being derived from an electrocardiographic signal detected by the sensor means at a time, defined by said regime data after a preceding detection of an electrocardiographic signal. The regime data may also include data defining the number of ECG data blocks to be recorded.

This embodiment enables a plurality of ECG monitoring operations to be performed at predetermined regular or irregular intervals without the need for the patient to constantly monitor the time. Thus, ECG recordings may be made at, for instance, hourly intervals during a critical period automatically once the patient has started the operation of the apparatus.

According to a second aspect of the present invention, there is provided a method of monitoring electrocardiographic signals, comprising the steps of:

(a) detecting operation of a user input means;
(b) detecting electrocardiographic signals for a predetermined period using means for detecting ECG signals;
(c) storing a block of ECG data representing electrocardiographic signals detected during the predetermined period in an IC card together with associated operation data representing operational parameters of the ECG signal detecting means;
(d) transferring the IC card to the data reading station; and
(e) reading the ECG data and operation data from the card.

Preferably, steps (a) to (c) are repeatedly performed before step (d) is performed. In this case, the following steps may be advantageously performed;
(f) if the user input means is operated for less than a predetermined duration, displaying the number of spaces available for ECG data blocks left on the IC card; and
(g) if the user input means is still being operated at the end of said predetermined duration continuing with step (b) until the end of the predetermined period else aborting step (b) and returning to step (a).

Preferably, the method includes the step of:
(h) applying two electrodes to a subject for carrying out step (b).

Preferably, the method includes the step of:
(i) detecting the impedance between the electrodes.

The impedance detection may take place at the beginning or end of said predetermined period. Data representing detected impedances is conveniently stored in the IC card as operation data.

Preferably, the method includes the step of:
(j) generating calibration data representing the calibration state of an ECG signal detecting means.

The calibration data is conveniently stored in the IC card as operation data.

Other operation data may be additionally or alternatively stored on the IC card. Such operation data may include the voltage level of a battery powering the means for detecting ECG signals or of one powering the IC card.

In an embodiment, step (a) includes reading regime data from the IC card and repeating steps (b) and (c) in dependence on said regime data.

According to a third aspect of the present invention, there is provided an ambulatory heart monitoring apparatus comprising: sensor means for detecting an electrocardiographic signal; interface means for receiving an IC card and for transferring data thereto; and control means responsive to operation of the user input means to cause a block of ECG data, derived from signals detected by the sensor means during a predetermined period to be sent to the interface means for storage on an IC card, characterised in that the control means sends an instrument ID code to the interface means for storage in the IC card.

According to a fourth aspect of the present invention, there is provided a method of monitoring electrocardiographic signals, comprising the steps of:
(a) detecting operation of a user input means;
(b) detecting electrocardiographic signals for a predetermined period using means for detecting ECG signals;
(c) storing a block of ECG data representing electrocardiographic Signals detected during the predetermined period in an IC card together with an instrument ID code;
(d) transferring the IC card to a data reading station; and
(e) reading the ECG data and intrument ID code from the card.

According to a fifth aspect of the present invention, there is provided an electrode comprising a flexible loop including a conductive portion, wherein the conductive portion forms at least part of a radially inwardly directed surface portion of the loop.

Preferably, the loop is formed from a strip of flexible material and fastener means, the fastener means being arranged for holding the strip in a loop.

Preferably, the loop is formed from silicone rubber.

Conveniently, the conductive portion is formed from an elastomer loaded with an electrically conducting substance. The conductive portion is preferably formed as a separate component and bonded to the loop material. However, it may be formed integrally with the loop material.

Preferably, the electrically conducting substance is nickel. However, other suitable electrically conducting substances, such as silver or carbon, may be used.

BRIEF DESCRIPTION OF THE DRAWINGS

An embodiment of the present invention will now be described, by way of example, with reference to the accompanying drawings, in which:

FIG. 3 shows a wriststrap electrode according to the third aspect of the present invention in its open condition;

FIG. 4 shows the electrode of FIG. 3 in its closed condition; and

FIG. 5 shows an apparatus according to the first aspect of the present invention combined with electrodes according to the second aspect of the present invention.

DETAILED DESCRIPTION

Figure 1:
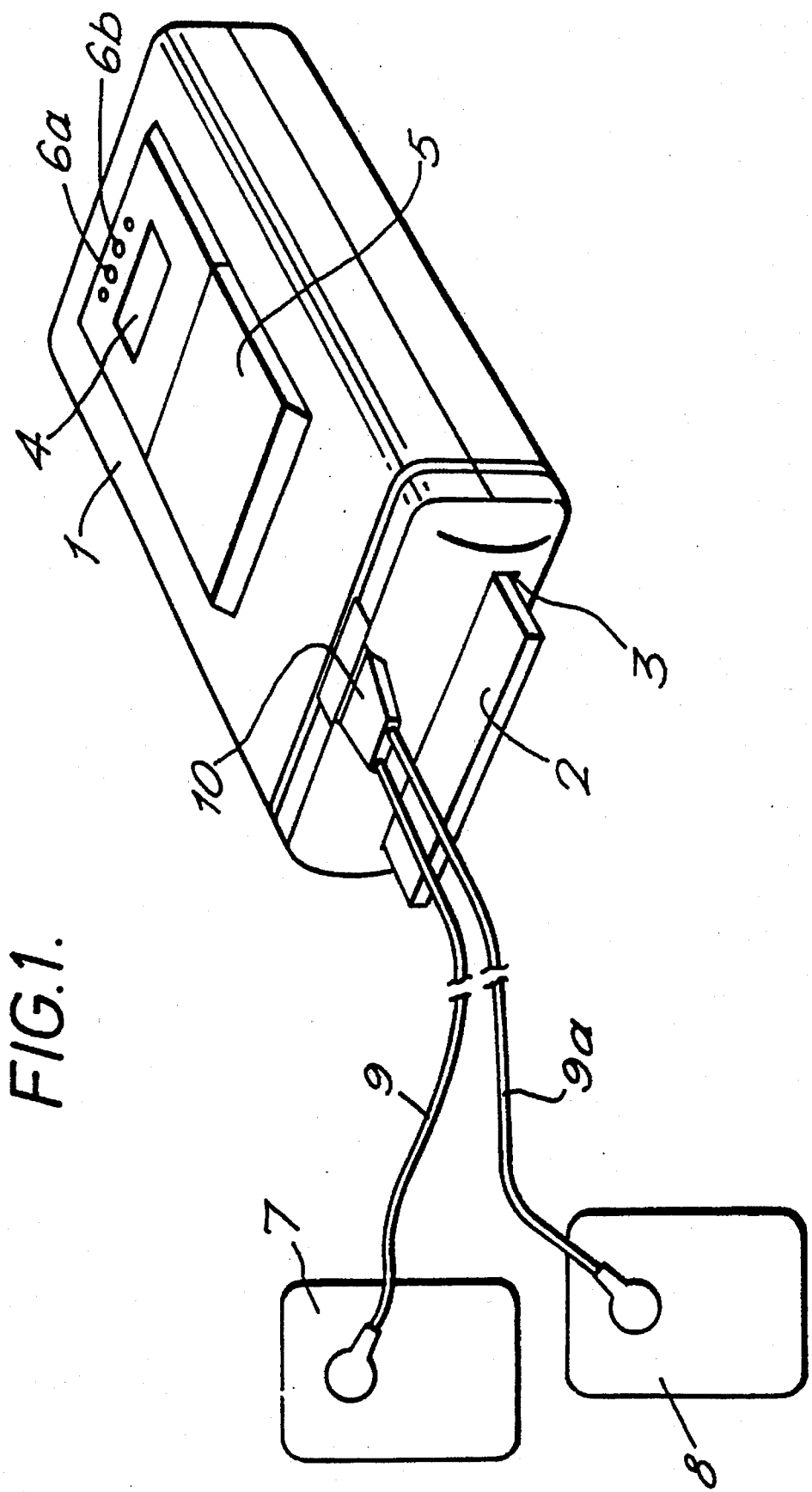
FIG. 1 shows an apparatus according to the first aspect of the present invention.

Referring to FIG. 1, a heart monitoring apparatus comprises a housing 1 which encloses the circuitry of the apparatus (not shown). An IC card 2 is received within a slot 3 in one wall of the housing 1. A four digit 7-segment liquid crystal display (LCD) 4 is mounted in another wall of the housing 1 together with a user input means, in the form of a double pole press-to-make switch 5, and a LED display 6 comprising a yellow LED 6a and a green LED 6b. A first electrode 7 and a second electrode 8 are coupled to the circuitry within the housing 1 by means of respective leads 9, 9a which go to a common plug 10.

Figure 2:
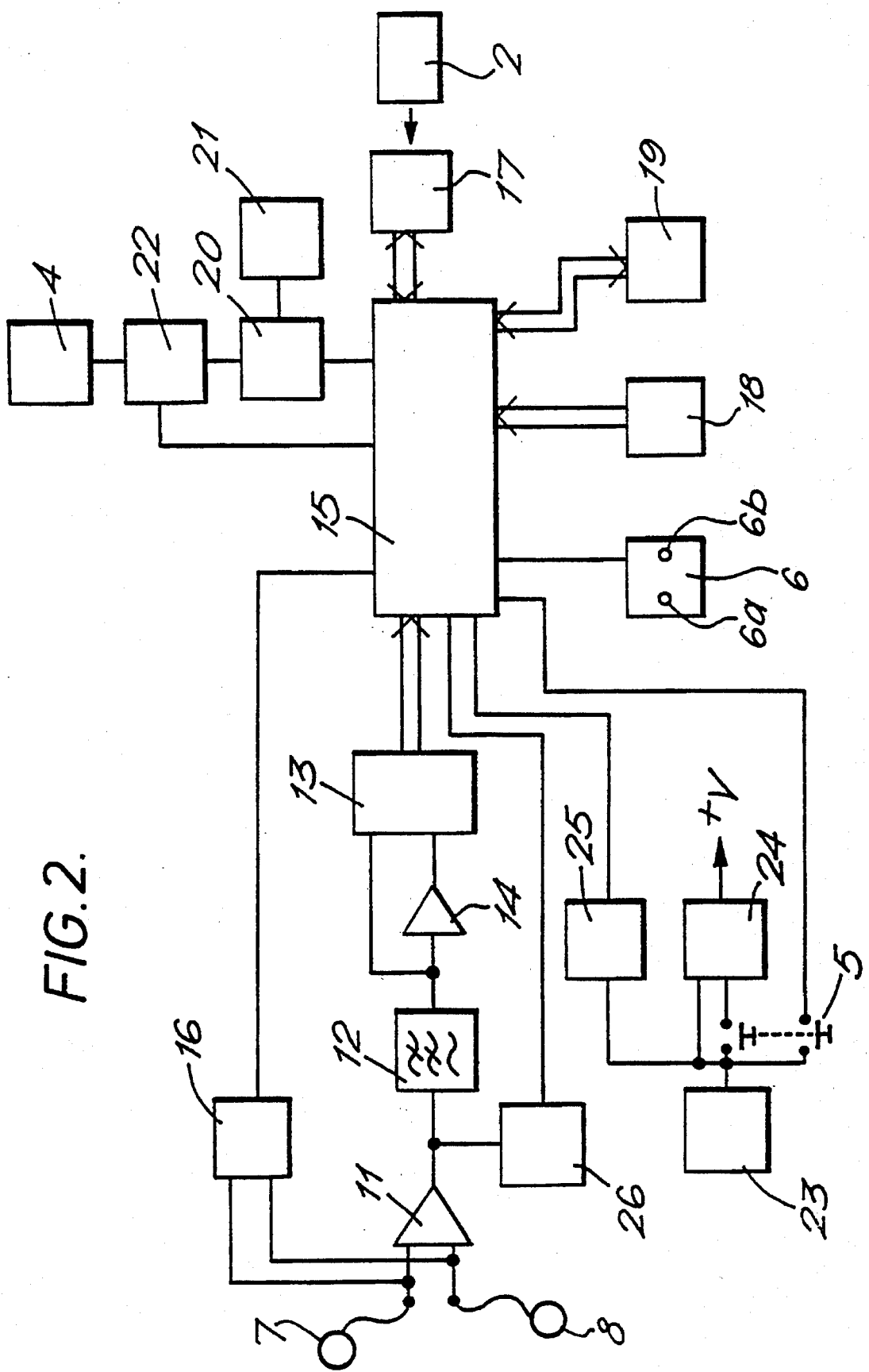
FIG. 2 is a block diagram of the electronic circuit of the apparatus shown in FIG. 1.

Referring to FIG. 2, the first and second electrodes 7, 8 are coupled to the input of a differential amplifier 11. The output of the differential amplifier 11 is fed to a filter 12. The filter 12 is a low-pass filter having a −3db point at approximately 40 Hz. The output of the filter is coupled to a first input of a multiplexing and analogue-to-digital converter circuit 13. The output of the filter 12 is also amplified by an amplifier 14 before being supplied to a second input of the multiplexer and analogue-to-digital converter circuit 13. The output of the multiplexing and analogue-to-digital converter circuit 13 is fed to a microprocessor 15 which controls the operation of the apparatus. The first and second electrodes 7, 8 are also coupled to the terminals of an impedance measuring circuit 16 which is driven by a signal from the microprocessor 15.

An output of the microprocessor 15 is coupled to a memory interface 17 which is arranged to receive an IC card 2. The microprocessor 15 is also coupled to the LED display 6, an EPROM 18, a RAM 19 and a real time clock circuit 20.

The real time clock 20 is powered by its own battery 21 and outputs time signals to a display interface 22 which drives the display 4. The display interface 22 is also coupled directly to the microprocessor 15.

Operating power for the apparatus is provided by a battery 23. Power is supplied to the functional blocks of the apparatus, including the microprocessor 15, from the battery 23 via a power control circuit 24. The power control circuit 24 is a latching circuit which operates to supply power to the microprocessor 15 on momentary operation of the switch 5, a first pole of which is connected between the battery 23 and a control input of the power control circuit 24.

A battery voltage sensing circuit 25 is arranged for detecting the voltage of the battery 23 and for providing a signal indicative of this voltage to the microprocessor 15.

The operation of the apparatus will now be described. The IC card 2 is inserted into the slot 3 until it is in operating relation with the memory interface 17. The subject then places the first and second electrodes 7, 8 on respective wrists.

Operation of the switch 5 causes the power control circuit 24 to supply power to the microprocessor 15. The microprocessor 15 then begins to perform a control program stored in the EPROM 18. The program stored in the EPROM 18 may make use of data in the IC card to control the operation of the apparatus. For instance, the microprocessor 15 may read sampling rate data from the IC card and use this to set the sampling rate of the analogue-to-digital converter circuit 13.

The device hardware is initialized by the microprocessor 15 which also lights the yellow LED 6a. There is then a short delay of approximately a third of a second, after which the microprocessor 15 applies a signal to the impedance measuring circuit 16. The impedance measuring circuit 16 injects a small current at 10 Hz through the electrodes 7, 8. The signal thus generated is amplified by the differential amplifier 11, filtered by the filter 12 and fed directly to the multiplexing and analogue-to-digital converter circuit 13. The microprocessor 15 monitors the output from the multiplexing and analogue-to-digital converter circuit 13 and determines an impedance value which is stored in the RAM 19. The impedance measurement is then terminated.

The microprocessor 15, then tests for the presence of an IC card 2 in the slot 3. If no card is detected, the yellow LED 6a is caused to flash for a period and the monitoring cycle of the device is terminated. If a card is, however, detected the microprocessor accesses the IC card 2 to read certain items of card specific data and any control data. In the embodiment described the card is pre-programmed with data representing a card ID number, a recording interval, the card size and a check sum. However, other data such as an A-to-D sampling rate may also be included. The recording interval sets the duration of an ECG monitoring operation. If the card has already received a recording it will include data indicating the number of recordings which have been made.

The microprocessor 15 first checks the check sum to ensure that the data read from the IC card 2 has not been corrupted and that the IC card 2 is of an appropriate type. From the card size and the number of recordings on the card, the microprocessor 15 calculates the number of recording spaces remaining on the card. This number is then sent, by the microprocessor 15, via the display interface 22 to be displayed on the display 4. If the IC card is found to be full, operation of the device is terminated and the yellow LED 6a is caused to flash for a period.

The microprocessor 15, then accepts a signal from the battery voltage sensor 25, indicating the initial battery voltage. If this voltage is below a predetermined level the microprocessor 15 causes the green LED 6b to flash to signal a low battery warning.

The microprocessor 15 then commences ECG signal monitoring.

The ECG signals picked up by the electrodes 7,8 are amplified by the differential amplifier 11 filtered by the filter 12 and then amplified by the amplifier 14 before being supplied to the multiplexer and analogue-to-digital circuit converter circuit 13. The microprocessor 15 takes the data output from the multiplexer and analogue-to-digital converter circuit 13 and stores it in the RAM 19.

The microprocessor 15 monitors the passage of time by monitoring the real time clock 20 and after a period of approximately three seconds from the operation of the switch 5, it checks whether the switch 5 is still being operated. This is performed by monitoring an input which is coupled to the battery 23 via a second pole of the switch 5. If the switch 5 has been released the microprocessor 15 sends a signal to the power control circuit 24 which causes the power control circuit 24 to interrupt the supply of power to the microprocessor 15, returning it to its dormant state.

If the switch 5 is indeed still being operated after three seconds, the ECG monitoring is continued until the end of the period, defined by the recording interval read from the IC card 2. The microprocessor 15 determines when the monitoring period is over with reference to the real time clock 20. Once the ECG monitoring has been completed the impedance between the electrodes 7,8 is again determined and the result stored in the RAM 19.

A calibration operation is then carried out. The microprocessor 15 supplies a signal to the calibrating circuit 26 which supplies a 1 millivolt peak-to-peak 2 Hz square wave to the input of the filter 12. The microprocessor 15 then detects the signal output by the multiplexing and analogue-to-digital converter circuit 13 and stores it in the RAM 19. This value gives an indication of the calibration state of the apparatus. The final battery voltage is then determined and stored in the RAM 19.

Finally, the microprocessor 15 transfers the data stored in the RAM 19, together with time and date data from the real time clock 20 and an instrument ID code from the EEPROM 18 to the memory interface 17 which outputs it to the IC card 2. The data output to the IC card 2 comprises the ECG signal data, calibration data, the initial impedance value, the final impedance value, the instrument ID code, a number representing the final battery voltage, a date code and a time code. Other data may be included as is deemed desirable. For instance, the state of the IC card battery may be monitored and data representing this may be stored on the IC card.

The subject can repeat the monitoring operation as the card capacity permits.

The subject may then remove the IC card from the housing 1, whereupon, the card can be transferred to a central station, e.g. by post, where it is read by a microcomputer system. The operation data, including the calibration data can be used as necessary to normalize the ECG data. The ECG data read from the IC card can be processed, stored, displayed or printed as required using conventional techniques.

The term "microprocessor" includes microcontrollers.

The impedance data and battery voltage data can be used in the management of a remote subject. For instance, if the battery voltage is low the subject may be instructed to replace the batteries. The impedance data indicates whether a subject is applying the electrodes properly. Therefore, if the measured impedance is high, it may indicate that the subject requires further tuition in how to use the apparatus.

In an alternative embodiment, the IC card 2 is preprogrammed with data defining a monitoring regime. This data may define an interval to separate periods of ECG monitoring and the number of monitoring operations to be performed.

This embodiment operates substantially in the same manner as the embodiment described above. However, following recording of a first block of ECG data, the microprocessor 15 continues to monitor the real time clock 20 and when it determines that a period, corresponding to the interval read from the IC card 2, has passed, starts a further ECG monitoring cycle. This process is repeated until the number of recordings made corresponds to the number read from the IC card 2.

Wriststrap electrodes 27, 28 will now be described in more detail with reference to FIGS. 3, 4 and 5.

Each electrode 27, 28 comprises a silicone rubber strip 30. The strip 30 is approximately 240 mm long. A first portion 30a of the strip 30 is approximately 25 mm wide and extends along approximately a third of the length of the strip from one end thereof. A second portion 30b, comprising the remainder of the strip, is approximately 16 mm wide. A buckle 31 is secured at the free end of the first portion 30a by means of a small tab 30c, extending therefrom.

A conductive portion 31, of substantially the same dimensions as the first portion 30a of the strip 30, is bonded to the first portion 30a of the strip 30. The conductive portion is formed from nickel loaded rubber.

A stud fastener 32 is located towards the free end of the first portion 30a of the strip 30 and holds the tab 30c in a loop so as to secure a buckle 34 to the strip 30. A rivet 33 is located towards the other end of the first portion 30a.

The electrode is formed into a loop by passing the free end of the second portion 30b of the strip 30 through the buckle. In use, a subject places the strip 30 about a wrist and tightens it by drawing the second portion 30b of the strip 30 through the buckle 34 so that the conducting portion 31 is in contact with his skin.

We claim:

1. An ambulatory heart monitoring apparatus comprising:
   sensor means for detecting an electrocardiographic signal;
   interface means for receiving an IC card and for transferring data thereto;
   user input means for inputting user commands;
   determining means for detecting operational parameters of the apparatus and producing operation data in dependence thereon; and
   control means responsive to operation of said user input means to cause a block of ECG data, derived from signals detected by said sensor means during a predetermined period, and said operation data to be sent to the interface means for storage in an IC card.

2. An apparatus according to claim 1, including means for producing calibration data representative of the calibration state of the apparatus, wherein said operation data includes said calibration data.

3. An apparatus according to claim 1, wherein the apparatus is powered by a battery and includes battery voltage sensing means, wherein said operation data includes data representing sensed battery voltage.

4. An apparatus according to claim 1, wherein the sensor means includes two electrodes for contacting the body of a patient and detecting means for detecting whether said electrodes are correctly contacting the body of a patient, and said operation data includes data indicative of whether said electrodes have correctly contacted the body of a patient during detection of an ECG signal.

5. An apparatus according to claim 4, wherein said detecting means comprises an impedance measuring means for measuring the impedance between said electrodes.

6. An apparatus according to claim 5, including means whereby the impedance between said electrodes is measured at the start and at the end of said predetermined period.

7. An apparatus according to claim 1, including an IC card, wherein the IC card is preprogrammed with data comprising a card ID, a recording period duration and the card capacity.

8. An apparatus according to claim 1, including an analogue-to-digital converter for digitizing signal output by said sensor means, wherein said control means is responsive to data from said interface means to control the sampling rate of said analogue-to-digital converter.

9. An apparatus according to claim 1, wherein said control means is responsive to regime data, stored on said IC card and supplied to said control means via said interface means to cause a further block of ECG data to be sent to said interface means, said further block of ECG data being derived from an electrocardiographic signal detected by said sensor means at a time, defined by said regime data, after a preceding detection of an electrocardiographic signal.

10. An apparatus according to claim 9, wherein the regime data includes data defining a number of ECG data blocks to be recorded.

11. A method of monitoring electrocardiographic signals, comprising the steps of:
   (a) detecting operation of a user input means;
   (b) detecting electrocardiographic signals for a predetermined period using means for detecting ECG signals;
   (c) storing a block of ECG data representing electrocardiographic signals detected during said predetermined period in an IC card together with associated operation data representing at least one operational parameter of the ECG signal detecting means;
   (d) transferring said IC card to a data reading station; and
   (e) reading said ECG data and said operation data from said card.

12. A method according to claim 11, wherein steps (a) to (c) are repeatedly performed before step (d) is performed.

13. A method according to claim 11, including the step of:
   (h) applying two electrodes to a patient for carrying out step (b).

14. A method according to claim 13, including the step of:
   (j) generating calibration data representing the calibration state of said ECG signal detecting means, wherein the operation data includes said calibration data.

15. A method according to claim 13, including the step of:
   (k) generating voltage data representative of the voltage of a battery powering said means for detecting ECG signals, wherein the operation data includes said voltage data.

16. A method according to claim 13, including the step of:
   (i) measuring the impedance between the electrodes.

17. A method according to claim 16, wherein impedance measurement takes place at the beginning and at the end of said predetermined period.

18. A method according to claim 16, wherein the operation data includes data representing a measured impedance.

19. A method according to claim 11, wherein step (a) includes reading regime data from said IC card and steps (b) and (c) are repeated in accordance with said regime.

20. A method of monitoring electrocardiographic signals, comprising the steps of:
   (a) detecting operation of a user input means;

(b) detecting electrocardiographic signals for a predetermined period using means for detecting ECG signals;

(c) storing a block of ECG data representing electrocardiographic signals detected during said predetermined period in an IC card together with associated operation data representing at least one operational parameter of the ECG signal detecting means;

(d) transferring said IC card to a data reading station;

(e) reading said ECG data and said operation data from said card, wherein steps (a) to (c) are repeatedly performed before step (d) is performed;

(f) if said user input means is operated for less than a predetermined duration, displaying the number of spaces available for ECG data blocks left on said IC card; and (g) if said user input means is still being operated at the end of said predetermined duration continuing with step (b) until the end of the predetermined period else aborting step (b) and returning to step (a).

21. An ambulatory heart monitoring apparatus comprising:

sensor means for detecting an electrocardiographic signal;

interface means for receiving an IC card and for transferring data thereto;

user input means for inputting user commands; and control means responsive to operation of said user input means to cause a block of ECG data, derived from signals detected by said sensor means during a predetermined period, and an instrument ID code to be sent to the interface means for storage in an IC card.

22. A method of monitoring electrocardiographic signals, comprising the steps of:

(a) detecting operation of a user input means;

(b) detecting electrocardiographic signals for a predetermined period using means for detecting ECG signals;

(c) storing a block of ECG data representing electrocardiographic signals detected during said predetermined period in an IC card together with an instrument ID code;

(d) transferring the IC card to a data reading station; and (e) reading the ECG data and instrument ID code from the card.

* * * * *